(12) United States Patent
Bianchi et al.

(10) Patent No.: US 12,274,514 B2
(45) Date of Patent: *Apr. 15, 2025

(54) GRAPHICAL USER INTERFACE FOR DISPLAYING GUIDANCE INFORMATION DURING AN IMAGE-GUIDED PROCEDURE

(71) Applicant: INTUITIVE SURGICAL OPERATIONS, INC., Sunnyvale, CA (US)

(72) Inventors: Cristian Bianchi, Capannori (IT); Vincent Duindam, San Francisco, CA (US); Oliver J. Wagner, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,346

(22) Filed: Oct. 6, 2023

(65) Prior Publication Data

US 2024/0033013 A1  Feb. 1, 2024

Related U.S. Application Data

(63) Continuation of application No. 16/310,804, filed as application No. PCT/US2017/040095 on Jun. 29, 2017, now Pat. No. 11,819,284.

(60) Provisional application No. 62/486,879, filed on Apr. 18, 2017, provisional application No. 62/357,217, filed on Jun. 30, 2016.

(51) Int. Cl.
*A61B 34/20* (2016.01)
*A61B 17/00* (2006.01)
(Continued)

(52) U.S. Cl.
CPC ........ *A61B 34/20* (2016.02); *A61B 17/00234* (2013.01); *A61B 34/35* (2016.02);
(Continued)

(58) Field of Classification Search
CPC ...... A61B 2034/301; A61B 2034/2061; A61B 2090/365; A61B 1/005; A61B 1/009
See application file for complete search history.

(56) References Cited

U.S. PATENT DOCUMENTS 5,638,619 A  6/1997 Manwaring et al.
6,346,940 B1  2/2002 Fukunaga
(Continued)

FOREIGN PATENT DOCUMENTS

CN  101854853 A  10/2010
CN  104780826 A  7/2015
(Continued)

OTHER PUBLICATIONS

Office Action for Chinese Application No. CN202111558845.9, mailed Dec. 9, 2023, 29 pages.
(Continued)

*Primary Examiner* — Ryan McCulley
(74) *Attorney, Agent, or Firm* — Haynes & Boone, LLP.

(57) ABSTRACT

A method for displaying guidance information during an image-guided surgical procedure comprises receiving, by one or more hardware processors, data from a tracking system associated with an elongate device comprising a flexible body and calculating, by the one or more hardware processors, at least one condition along a length of the flexible body based on the data. The method further comprises determining, by the one or more hardware processors, supplemental guidance information based on the at least one condition and augmenting, by the one or more hardware processors, one or more images with the supplemental guidance information to produce one or more augmented images. The method further comprises displaying the one or more augmented images on a display device at a surgeon console.

15 Claims, 9 Drawing Sheets

(51) Int. Cl.
  *A61B 34/10*  (2016.01)
  *A61B 34/35*  (2016.01)
  *A61B 90/00*  (2016.01)
  *A61M 25/01*  (2006.01)
  *G06T 19/00*  (2011.01)
  *G06T 19/20*  (2011.01)

(52) U.S. Cl.
  CPC ....... *A61M 25/0105* (2013.01); *G06T 19/003* (2013.01); *G06T 19/006* (2013.01); *G06T 19/20* (2013.01); *A61B 2017/00115* (2013.01); *A61B 2017/00199* (2013.01); *A61B 2017/003* (2013.01); *A61B 2034/101* (2016.02); *A61B 2034/2055* (2016.02); *A61B 2034/2061* (2016.02); *A61B 2090/365* (2016.02); *A61M 2025/0166* (2013.01); *G06T 2219/2012* (2013.01)

(56) References Cited

U.S. PATENT DOCUMENTS

| | | | |
|---|---|---|---|
| 6,380,732 B1 | 4/2002 | Gilboa | |
| 6,389,187 B1 | 5/2002 | Greenaway et al. | |
| 6,432,041 B1 | 8/2002 | Taniguchi et al. | |
| 6,671,538 B1 | 12/2003 | Ehnholm et al. | |
| 7,316,681 B2 | 1/2008 | Madhani et al. | |
| 7,772,541 B2 | 8/2010 | Froggatt et al. | |
| 7,930,065 B2 | 4/2011 | Larkin et al. | |
| 8,218,846 B2 | 7/2012 | Trumer et al. | |
| 8,412,307 B2 | 4/2013 | Willis et al. | |
| 8,672,836 B2 | 3/2014 | Higgins et al. | |
| 8,900,131 B2 | 12/2014 | Chopra et al. | |
| 9,259,274 B2 | 2/2016 | Prisco | |
| 9,326,680 B2 | 5/2016 | Akimoto et al. | |
| 9,452,276 B2 | 9/2016 | Duindam et al. | |
| 9,603,668 B2 | 3/2017 | Weingarten et al. | |
| 11,612,384 B2 | 3/2023 | Duindam et al. | |
| 11,819,284 B2 | 11/2023 | Bianchi et al. | |
| 2002/0049375 A1 | 4/2002 | Strommer et al. | |
| 2004/0082849 A1 | 4/2004 | Schweikard et al. | |
| 2004/0165810 A1 | 8/2004 | Fujita | |
| 2005/0182295 A1 | 8/2005 | Soper et al. | |
| 2005/0261550 A1 | 11/2005 | Akimoto et al. | |
| 2006/0013523 A1 | 1/2006 | Childers et al. | |
| 2007/0065077 A1 | 3/2007 | Childers et al. | |
| 2007/0270650 A1 | 11/2007 | Eno et al. | |
| 2007/0293721 A1 | 12/2007 | Gilboa | |
| 2008/0183190 A1 | 7/2008 | Adcox et al. | |
| 2008/0275467 A1 | 11/2008 | Liao et al. | |
| 2009/0156895 A1 | 6/2009 | Higgins et al. | |
| 2009/0198104 A1 | 8/2009 | Sugiyama | |
| 2009/0227861 A1 | 9/2009 | Ganatra et al. | |
| 2009/0326553 A1 | 12/2009 | Mustufa et al. | |
| 2010/0076305 A1 | 3/2010 | Maier-Hein et al. | |
| 2010/0141675 A1 | 6/2010 | Matsumoto | |
| 2010/0179418 A1 | 7/2010 | Mueller et al. | |
| 2010/0217117 A1 | 8/2010 | Glossop et al. | |
| 2010/0249506 A1 | 9/2010 | Prisco | |
| 2010/0317965 A1 | 12/2010 | Itkowitz et al. | |
| 2011/0234780 A1 | 9/2011 | Ito et al. | |
| 2011/0319815 A1 | 12/2011 | Roelle et al. | |
| 2012/0065481 A1 | 3/2012 | Hunter et al. | |
| 2012/0089022 A1 | 4/2012 | House et al. | |
| 2012/0120091 A1 | 5/2012 | Koudijs et al. | |
| 2012/0289843 A1 | 11/2012 | Chopra et al. | |
| 2013/0179820 A1 | 7/2013 | Asami et al. | |
| 2013/0204124 A1 | 8/2013 | Duindam et al. | |
| 2013/0223702 A1 | 8/2013 | Holsing et al. | |
| 2013/0281838 A1 | 10/2013 | Trumer et al. | |
| 2013/0345719 A1 | 12/2013 | Donhowe et al. | |
| 2014/0142422 A1 | 5/2014 | Manzke et al. | |
| 2014/0188440 A1 | 7/2014 | Donhowe et al. | |
| 2014/0211213 A1 | 7/2014 | Weiss | |
| 2014/0221921 A1 | 8/2014 | Gilboa et al. | |
| 2014/0350391 A1 | 11/2014 | Prisco et al. | |
| 2015/0073265 A1 | 3/2015 | Popovic et al. | |
| 2015/0297864 A1* | 10/2015 | Kokish | A61B 34/37 604/95.04 |
| 2016/0000302 A1 | 1/2016 | Brown et al. | |
| 2016/0000356 A1 | 1/2016 | Brown et al. | |
| 2016/0000517 A1 | 1/2016 | Kehat et al. | |
| 2016/0070878 A1 | 3/2016 | Soper et al. | |
| 2016/0073928 A1 | 3/2016 | Soper et al. | |
| 2016/0183841 A1 | 6/2016 | Duindam et al. | |
| 2016/0300017 A1 | 10/2016 | Lee et al. | |
| 2016/0371883 A1 | 12/2016 | Merkine et al. | |
| 2017/0071504 A1 | 3/2017 | Wang | |
| 2017/0084027 A1 | 3/2017 | Mintz et al. | |
| 2017/0151027 A1 | 6/2017 | Walker et al. | |
| 2017/0281047 A1* | 10/2017 | Yamamoto | A61B 1/00045 |
| 2018/0177383 A1 | 6/2018 | Noonan et al. | |
| 2018/0185100 A1 | 7/2018 | Weinstein et al. | |
| 2020/0030044 A1 | 1/2020 | Wang et al. | |
| 2020/0054399 A1 | 2/2020 | Duindam et al. | |
| 2020/0129239 A1 | 4/2020 | Bianchi et al. | |
| 2023/0200790 A1 | 6/2023 | Duindam et al. | |

FOREIGN PATENT DOCUMENTS

| | | |
|---|---|---|
| CN | 105193503 A | 12/2015 |
| CN | 105636541 A | 6/2016 |
| CN | 106232001 A | 12/2016 |
| EP | 1103229 A2 | 5/2001 |
| EP | 2085017 A1 | 8/2009 |
| EP | 3478161 A1 | 5/2019 |
| JP | H08332191 A | 12/1996 |
| JP | 2004506466 A | 3/2004 |
| JP | 2004513684 A | 5/2004 |
| JP | 2008000261 A | 1/2008 |
| JP | 2015518987 A | 7/2015 |
| JP | 2016030125 A | 3/2016 |
| WO | WO-9729709 A1 | 8/1997 |
| WO | WO-0215775 A2 | 2/2002 |
| WO | WO-2007047782 A2 | 4/2007 |
| WO | WO-2007146987 A2 | 12/2007 |
| WO | WO-2008125910 A1 | 10/2008 |
| WO | WO-2009138871 A2 | 11/2009 |
| WO | WO-2011043982 A1 | 4/2011 |
| WO | WO-2012158324 A2 | 11/2012 |
| WO | WO-2014028394 A1 | 2/2014 |
| WO | WO-2014139022 A1 | 9/2014 |
| WO | WO-2014141968 A1 | 9/2014 |
| WO | WO-2015023665 A1 | 2/2015 |
| WO | WO-2015164587 A2 | 10/2015 |
| WO | WO-2016004007 A1 | 1/2016 |
| WO | WO-2016018646 A1 | 2/2016 |
| WO | WO-2016018648 A1 | 2/2016 |
| WO | WO-2016032846 A1 | 3/2016 |
| WO | WO-2016040080 A1 | 3/2016 |
| WO | WO-2018005680 A1 | 1/2018 |
| WO | WO-2018005842 A1 | 1/2018 |

OTHER PUBLICATIONS

Extended European Search Report for Application No. EP14836490.4, mailed on Mar. 24, 2017, 9 pages.
Extended European Search Report for Application No. EP17821278 mailed on Jan. 23, 2020, 12 pages.
Extended European Search Report for Application No. EP17821289 mailed on Feb. 7, 2020, 9 pages.
Extended European Search Report for Application No. EP18787852.5 mailed on Mar. 5, 2021, 14 pages.
Extended European Search Report for Application No. EP23182322.0, mailed on Oct. 2, 2023, 11 pages.
International Preliminary Report on Patentability for Application No. PCT/US2014/050715, mailed on Feb. 25, 2016, 14 pages.
International Preliminary Report on Patentability for Application No. PCT/US2018/028190, mailed on Oct. 31, 2019, 11 pages.
International Preliminary Reporton Patentability for Application No. PCT/US2017/040095, mailed on Jan. 10, 2019, 8 pages.

(56) References Cited

OTHER PUBLICATIONS

International Search Report and Written Opinion for Application No. PCT/US2014/050715, mailed on Nov. 13, 2014, 17 pages.
International Search Report and Written Opinion for Application No. PCT/US2017/040067, mailed on Aug. 30, 2017, 13 pages.
International Search Report and Written Opinion for Application No. PCT/US2017/040095, mailed on Nov. 10, 2017, 11 pages.
International Search Report and Written Opinion for Application No. PCT/US2018/028190, mailed on Aug. 3, 2018, 14 pages.
Keller S.G., et al., "Equivalent Stress and Strain Distribution in Helical Compression Springs Subjected to Bending," The Journal of Strain Analysis for Engineering Design, Aug. 2011, vol. 46 (6), pp. 405-415.
Office Action for Chinese Application No. CN20188030958, mailed Apr. 14, 2023, 27 pages.
Office Action for Chinese Application No. CN20188030958, mailed Aug. 24, 2022, 21 pages.
Office Action for Chinese Application No. CN20188030958. mailed Sep. 16, 2023. 18 pages.
Office Action mailed Apr. 8, 2021 for Chinese Application No. 201780039120 filed Jun. 29, 2017, 28 pages.
Partial Supplementary European Search Report for Application No. EP18787852.5 mailed on Dec. 2, 2020, 17 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP24170572.2, mailed on Jul. 10, 2024, 11 pages.

* cited by examiner

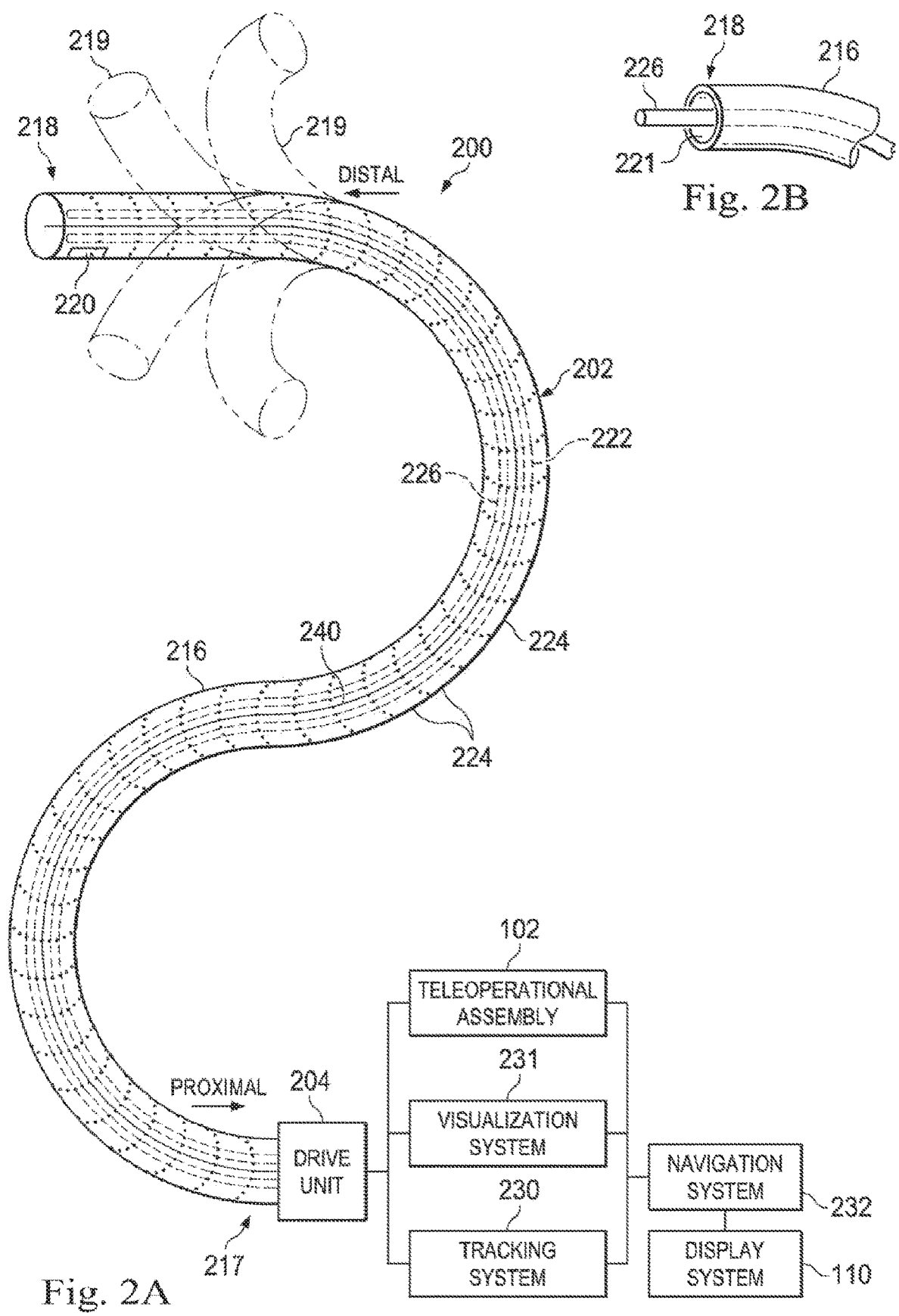

GRAPHICAL USER INTERFACE FOR DISPLAYING GUIDANCE INFORMATION DURING AN IMAGE-GUIDED PROCEDURE

RELATED APPLICATIONS

This patent application is the continuation of U.S. patent application Ser. No. 16/310,804 entitled "Graphical User Interface for Monitoring an Image-Guided Procedure," filed Dec. 17, 2018, which was the U.S. national phase of International Application No. PCT/US2017/040095, filed Jun. 29, 2017, which designated the U.S. and claims priority to and the benefit of the filing date of U.S. Provisional Patent Application No. 62/486,879 entitled "Graphical User Interface for Monitoring an Image-Guided Procedure," filed Apr. 18, 2017 and to U.S. Provisional Patent Application No. 62/357,217 entitled "Graphical User Interface for Displaying Guidance Information During an Image-Guided Procedure" filed Jun. 30, 2016, each of which is incorporated by reference herein in its entirety. The present disclosure is related to U.S. Provisional Patent Application 62/357,258, entitled "Graphical User Interface for Displaying Guidance Information in a Plurality of Modes During an Image-Guided Procedure," filed Jun. 30, 2016; U.S. Provisional Patent Application 62/357,272, entitled "Systems and Methods of Steerable Elongate Device," filed Jun. 30, 2016; and PCT/US2017/039808, entitled "Systems and Methods of Steerable Elongate Device," filed Jun. 28, 2017, which are hereby incorporated by reference in their entirety.

TECHNICAL FIELD

The present disclosure is directed to systems and methods for conducting an image-guided procedure and more particularly to systems and methods for displaying guidance information during an image-guided procedure.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions clinicians may insert minimally invasive medical instruments (including surgical, diagnostic, therapeutic, or biopsy instruments) to reach a target tissue location. One such minimally invasive technique is to use a flexible and/or steerable elongate device, such as a catheter, that can be inserted into anatomic passageways and navigated toward a region of interest within the patient anatomy. Control of such an elongate device by medical personnel during an image-guided procedure involves the management of several degrees of freedom including at least the management of insertion and retraction of the elongate device as well as steering and/or bend radius of the device. In addition, different modes of operation may also be supported.

Accordingly, it would be advantageous to provide a graphical user interface that supports intuitive control and management of flexible and/or steerable elongate devices, such as steerable catheters, that are suitable for use during minimally invasive medical techniques.

SUMMARY

The embodiments of the invention are best summarized by the claims that follow the description.

A method for displaying guidance information during an image-guided surgical procedure comprises receiving, by one or more hardware processors, data from a tracking system associated with an elongate device comprising a flexible body and calculating, by the one or more hardware processors, at least one condition along a length of the flexible body based on the data. The method further comprises determining, by the one or more hardware processors, supplemental guidance information based on the at least one condition and augmenting, by the one or more hardware processors, one or more images with the supplemental guidance information to produce one or more augmented images. The method further comprises displaying the one or more augmented images on a display device at a surgeon console. A non-transitory machine-readable medium comprises a plurality of machine-readable instructions which when executed by one or more processors associated with the medical device are adapted to cause the one or more processors to perform the method for displaying guidance information.

A medical device comprising an elongate device including a flexible body and a tracking system disposed along at least a portion of the flexible body. The medical system also comprises one or more processors coupled to the tracking system. The one or more processors are configured to receive data from the tracking system, calculate at least one condition along a length of the flexible body based on the received data, and determine supplemental guidance information based on the at least one condition. The one or more processors are further configured to augment one or more images using the supplemental guidance information to produce one or more augmented images and display the one or more augmented images.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

FIG. 2A is a simplified diagram of a medical instrument system according to some embodiments.

FIG. 2B is a simplified diagram of a medical instrument with an extended medical tool according to some embodiments.

Figure 1:
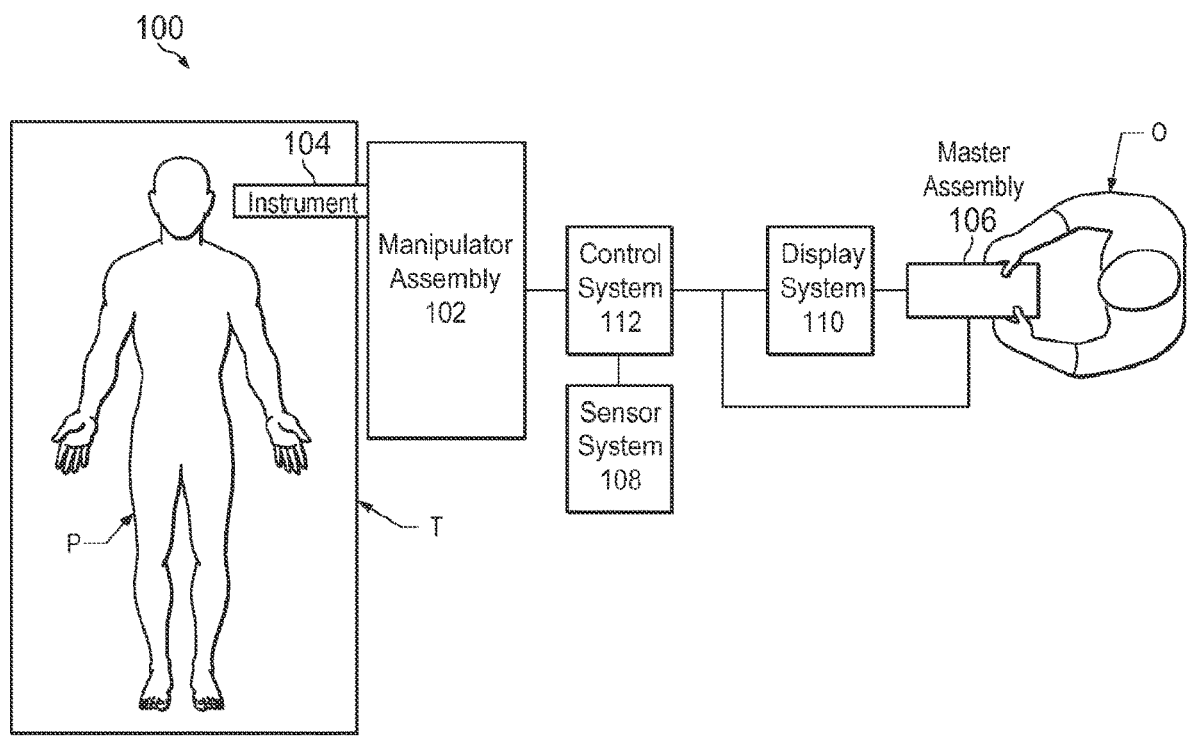
FIG. 1 is a simplified diagram of a teleoperated medical system according to some embodiments.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

FIG. 1 is a simplified diagram of a teleoperated medical system 100 (also called "teleoperational manipulator assembly") according to some embodiments. In some embodiments, teleoperated medical system 100 may be suitable for use in, for example, surgical, diagnostic, therapeutic, or biopsy procedures. As shown in FIG. 1, medical system 100 generally includes a teleoperational manipulator assembly 102 for operating a medical instrument 104 in performing various procedures on a patient P. Teleoperational manipulator assembly 102 is mounted to or near an operating table T. A master assembly 106 allows an operator (e.g., a surgeon, a clinician, or a physician O as illustrated in FIG. 1) to view the interventional site and to control teleoperational manipulator assembly 102.

Master assembly 106 may be located at a surgeon's console which is usually located in the same room as operating table T, such as at the side of a surgical table on which patient P is located. However, it should be understood that physician O can be located in a different room or a completely different building from patient P. Master assembly 106 generally includes one or more control devices for controlling teleoperational manipulator assembly 102. The control devices may include any number of a variety of input devices, such as joysticks, trackballs, data gloves, trigger-guns, hand-operated controllers, voice recognition devices, body motion or presence sensors, and/or the like. To provide physician O a strong sense of directly controlling instruments 104 the control devices may be provided with the same degrees of freedom as the associated medical instrument 104. In this manner, the control devices provide physician O with telepresence or the perception that the control devices are integral with medical instruments 104.

In some embodiments, the control devices may have more or fewer degrees of freedom than the associated medical instrument 104 and still provide physician O with telepresence. In some embodiments, the control devices may optionally be manual input devices which move with six degrees of freedom, and which may also include an actuatable handle for actuating instruments (for example, for closing grasping jaws, applying an electrical potential to an electrode, delivering a medicinal treatment, and/or the like).

Teleoperational manipulator assembly 102 supports medical instrument 104 and may include a kinematic structure of one or more non-servo controlled links (e.g., one or more links that may be manually positioned and locked in place, generally referred to as a set-up structure) and a teleoperational manipulator. Teleoperational manipulator assembly 102 may optionally include a plurality of actuators or motors that drive inputs on medical instrument 104 in response to commands from the control system (e.g., a control system 112). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to medical system 100 describing the rotation and orientation of the motor shafts. This position sensor data may be used to determine motion of the objects manipulated by the actuators.

Teleoperated medical system 100 may include a sensor system 108 with one or more sub-systems for receiving information about the instruments of teleoperational manipulator assembly 102. Such sub-systems may include a position/location sensor system (e.g., an electromagnetic (EM) sensor system); a shape sensor system for determining the position, orientation, speed, velocity, pose, and/or shape of a distal end and/or of one or more segments along a flexible body that may make up medical instrument 104; and/or a visualization system for capturing images from the distal end of medical instrument 104.

Teleoperated medical system 100 also includes a display system 110 for displaying an image or representation of the surgical site and medical instrument 104 generated by subsystems of sensor system 108. Display system 110 and master assembly 106 may be oriented so physician O can control medical instrument 104 and master assembly 106 with the perception of telepresence.

In some embodiments, medical instrument 104 may have a visualization system (discussed in more detail below), which may include a viewing scope assembly that records a concurrent or real-time image of a surgical site and provides the image to the operator or physician O through one or more displays of medical system 100, such as one or more displays of display system 110. The concurrent image may be, for example, a two or three dimensional image captured by an endoscope positioned within the surgical site. In some embodiments, the visualization system includes endoscopic components that may be integrally or removably coupled to medical instrument 104. However in some embodiments, a separate endoscope, attached to a separate manipulator assembly may be used with medical instrument 104 to image the surgical site. The visualization system may be implemented as hardware, firmware, software or a combination thereof which interact with or are otherwise executed by one or more computer processors, which may include the processors of a control system 112.

Display system 110 may also display an image of the surgical site and medical instruments captured by the visualization system. In some examples, teleoperated medical system 100 may configure medical instrument 104 and controls of master assembly 106 such that the relative positions of the medical instruments are similar to the relative positions of the eyes and hands of physician O. In this manner physician O can manipulate medical instrument 104 and the hand control as if viewing the workspace in substantially true presence. By true presence, it is meant that the presentation of an image is a true perspective image simulating the viewpoint of a physician that is physically manipulating medical instrument 104.

In some examples, display system 110 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. The pre-operative or intra-operative image data may be presented as two-dimensional, three-dimensional, or four-dimensional (including e.g., time based or velocity based information) images and/or as images from models created from the pre-operative or intra-operative image data sets.

In some embodiments, often for purposes of imaged guided surgical procedures, display system 110 may display a virtual navigational image in which the actual location of medical instrument 104 is registered (i.e., dynamically referenced) with the preoperative or concurrent images/model. This may be done to present the physician O with a virtual image of the internal surgical site from a viewpoint of medical instrument 104. In some examples, the viewpoint may be from a tip of medical instrument 104. An image of the tip of medical instrument 104 and/or other graphical or alphanumeric indicators may be superimposed on the virtual image to assist physician O controlling medical instrument 104. In some examples, medical instrument 104 may not be visible in the virtual image.

In some embodiments, display system 110 may display a virtual navigational image in which the actual location of medical instrument 104 is registered with preoperative or concurrent images to present the physician O with a virtual image of medical instrument 104 within the surgical site from an external viewpoint. An image of a portion of medical instrument 104 or other graphical or alphanumeric indicators may be superimposed on the virtual image to assist physician in the control of medical instrument 104. As described herein, visual representations of data points may be rendered to display system 110. For example, measured data points, moved data points, registered data points, and other data points described herein may be displayed on display system 110 in a visual representation. The data points may be visually represented in a user interface by a plurality of points or dots on display system 110 or as a rendered model, such as a mesh or wire model created based on the set of data points. In some examples, the data points may be color coded according to the data they represent. In some embodiments, a visual representation may be refreshed in display system 110 after each processing operation has been implemented to alter data points.

Teleoperated medical system 100 may also include control system 112. Control system 112 includes at least one memory and at least one computer processor (not shown) for effecting control between medical instrument 104, master assembly 106, sensor system 108, and display system 110. Control system 112 also includes programmed instructions (e.g., a non-transitory machine-readable medium storing the instructions) to implement some or all of the methods described in accordance with aspects disclosed herein, including instructions for providing information to display system 110. While control system 112 is shown as a single block in the simplified schematic of FIG. 1, the system may include two or more data processing circuits with one portion of the processing optionally being performed on or adjacent to teleoperational manipulator assembly 102, another portion of the processing being performed at master assembly 106, and/or the like. The processors of control system 112 may execute instructions comprising instruction corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 112 supports wireless communication protocols such as Bluetooth, IrDA, HomeRF, IEEE 802.11, DECT, and Wireless Telemetry.

In some embodiments, control system 112 may receive force and/or torque feedback from medical instrument 104. Responsive to the feedback, control system 112 may transmit signals to master assembly 106. In some examples, control system 112 may transmit signals instructing one or more actuators of teleoperational manipulator assembly 102 to move medical instrument 104. Medical instrument 104 may extend into an internal surgical site within the body of patient P via openings in the body of patient P. Any suitable conventional and/or specialized actuators may be used. In some examples, the one or more actuators may be separate from, or integrated with, teleoperational manipulator assembly 102. In some embodiments, the one or more actuators and teleoperational manipulator assembly 102 are provided as part of a teleoperational cart positioned adjacent to patient P and operating table T.

Control system 112 may optionally further include a virtual visualization system to provide navigation assistance to physician O when controlling medical instrument 104 during an image-guided surgical procedure. Virtual navigation using the virtual visualization system may be based upon reference to an acquired preoperative or intraoperative dataset of anatomic passageways. The virtual visualization system processes images of the surgical site imaged using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like. Software, which may be used in combination with manual inputs, is used to convert the recorded images into segmented two dimensional or three dimensional composite representation of a partial or an entire anatomic organ or anatomic region. An image data set is associated with the composite representation. The composite representation and the image data set describe the various locations and shapes of the passageways and their connectivity. The images used to generate the composite representation may be recorded preoperatively or intra-operatively during a clinical procedure. In some embodiments, a virtual visualization system may use standard representations (i.e., not patient specific) or hybrids of a standard representation and patient specific data. The composite representation and any virtual images generated by the composite representation may represent the static posture of a deformable anatomic region during one or more phases of motion (e.g., during an inspiration/expiration cycle of a lung).

During a virtual navigation procedure, sensor system 108 may be used to compute an approximate location of medical instrument 104 with respect to the anatomy of patient P. The location can be used to produce both macro-level (external) tracking images of the anatomy of patient P and virtual internal images of the anatomy of patient P. The system may implement one or more electromagnetic (EM) sensor, fiber optic sensors, and/or other sensors to register and display a medical implement together with preoperatively recorded surgical images, such as those from a virtual visualization system, are known. For example U.S. patent application Ser. No. 13/107,562 (filed May 13, 2011) (disclosing "Medical System Providing Dynamic Registration of a Model of an Anatomic Structure for Image-Guided Surgery") which is incorporated by reference herein in its entirety, discloses one such system. Teleoperated medical system 100 may further include optional operations and support systems (not shown) such as illumination systems, steering control systems, irrigation systems, and/or suction systems. In some embodiments, teleoperated medical system 100 may include more than one teleoperational manipulator assembly and/or more than one master assembly. The exact number of teleoperational manipulator assemblies will depend on the surgical procedure and the space constraints within the operating room, among other factors. Master assembly 106 may be collocated or they may be positioned in separate locations. Multiple master assemblies allow more than one operator to control one or more teleoperational manipulator assemblies in various combinations.

FIG. 2A is a simplified diagram of a medical instrument system 200 according to some embodiments. In some embodiments, medical instrument system 200 may be used as medical instrument 104 in an image-guided medical procedure performed with teleoperated medical system 100. In some examples, medical instrument system 200 may be used for non-teleoperational exploratory procedures or in procedures involving traditional manually operated medical instruments, such as endoscopy. Optionally medical instrument system 200 may be used to gather (i.e., measure) a set of data points corresponding to locations within anatomic passageways of a patient, such as patient P.

Medical instrument system 200 includes elongate device 202 coupled to a drive unit 204. Elongate device 202 includes a flexible body 216 having proximal end 217 and distal end 218 (also called "tip portion 218"). In some embodiments, flexible body 216 has an approximately 3 mm outer diameter. Other flexible body outer diameters may be larger or smaller.

Medical instrument system 200 further includes a tracking system 230 for determining the position, orientation, speed, velocity, pose, and/or shape of flexible body 216 at distal end 218 and/or of one or more segments 224 along flexible body 216 using one or more sensors and/or imaging devices as described in further detail below. The entire length of flexible body 216, between distal end 218 and proximal end 217, may be effectively divided into segments 224. If medical instrument system 200 is consistent with medical instrument 104 of a teleoperated medical system 100, tracking system 230. Tracking system 230 may optionally be implemented as hardware, firmware, software or a combination thereof which interact with or are otherwise executed by one or more computer processors, which may include the processors of control system 112 in FIG. 1.

Tracking system 230 may optionally track distal end 218 and/or one or more of the segments 224 using a shape sensor 222. Shape sensor 222 may optionally include an optical fiber aligned with flexible body 216 (e.g., provided within an interior channel (not shown) or mounted externally). In one embodiment, the optical fiber has a diameter of approximately 200 μm. In other embodiments, the dimensions may be larger or smaller. The optical fiber of shape sensor 222 forms a fiber optic bend sensor for determining the shape of flexible body 216. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389 (filed Jul. 13, 2005) (disclosing "Fiber optic position and shape sensing device and method relating thereto"); U.S. patent application Ser. No. 12/047,056 (filed on Jul. 16, 2004) (disclosing "Fiber-optic shape and relative position sensing"); and U.S. Pat. No. 6,389,187 (filed on Jun. 17, 1998) (disclosing "Optical Fibre Bend Sensor"), which are all incorporated by reference herein in their entireties. Sensors in some embodiments may employ other suitable strain sensing techniques, such as Rayleigh scattering, Raman scattering, Brillouin scattering, and Fluorescence scattering. In some embodiments, the shape of flexible body 216 may be determined using other techniques. For example, a history of the distal end pose of flexible body 216 can be used to reconstruct the shape of flexible body 216 over the interval of time. In some embodiments, tracking system 230 may optionally and/or additionally track distal end 218 using a position sensor system 220. Position sensor system 220 may comprise, or be a component of, an EM sensor system including one or more conductive coils that may be subjected to an externally generated electromagnetic field. Each coil of an EM sensor system used to implement position sensor system 220 then produces an induced electrical signal having characteristics that depend on the position and orientation of the coil relative to the externally generated electromagnetic field. In some embodiments, position sensor system 220 may be configured and positioned to measure six degrees of freedom, e.g., three position coordinates X, Y, Z and three orientation angles indicating pitch, yaw, and roll of a base point or five degrees of freedom, e.g., three position coordinates X, Y, Z and two orientation angles indicating pitch and yaw of a base point. Further description of a position sensor system is provided in U.S. Pat. No. 6,380,732 (filed Aug. 11, 1999) (disclosing "Six-Degree of Freedom Tracking System Having a Passive Transponder on the Object Being Tracked"), which is incorporated by reference herein in its entirety.

In some embodiments, tracking system 230 may alternately and/or additionally rely on historical pose, position, or orientation data stored for a known point of an instrument system along a cycle of alternating motion, such as breathing. This stored data may be used to develop shape information about flexible body 216. In some examples, a series of positional sensors (not shown), such as electromagnetic (EM) sensors similar to the sensors in position sensor system 220 may be positioned along flexible body 216 and then used for shape sensing. In some examples, a history of data from one or more of these sensors taken during a procedure may be used to represent the shape of elongate device 202, particularly if an anatomic passageway is generally static.

Flexible body 216 includes a channel 221 sized and shaped to receive a medical instrument 226. FIG. 2B is a simplified diagram of flexible body 216 with medical instrument 226 extended according to some embodiments. In some embodiments, medical instrument 226 may be used for procedures such as surgery, biopsy, ablation, illumination, irrigation, or suction. Medical instrument 226 can be deployed through channel 221 of flexible body 216 and used at a target location within the anatomy. Medical instrument 226 may include, for example, image capture probes, biopsy instruments, laser ablation fibers, and/or other surgical, diagnostic, or therapeutic tools. Medical tools may include end effectors having a single working member such as a scalpel, a blunt blade, an optical fiber, an electrode, and/or the like. Other end effectors may include, for example, forceps, graspers, scissors, clip appliers, and/or the like. Other end effectors may further include electrically activated end effectors such as electrosurgical electrodes, transducers, sensors, and/or the like. In various embodiments, medical instrument 226 is a biopsy instrument, which may be used to remove sample tissue or a sampling of cells from a target anatomic location. Medical instrument 226 may be used with an image capture probe also within flexible body 216. In various embodiments, medical instrument 226 may be an image capture probe that includes a distal portion with a stereoscopic or monoscopic camera at or near distal end 218 of flexible body 216 for capturing images (including video images) that are processed by a visualization system 231 for display and/or provided to tracking system 230 to support tracking of distal end 218 and/or one or more of the segments 224. The image capture probe may include a cable coupled to the camera for transmitting the captured image data. In some examples, the image capture instrument may be a fiber-optic bundle, such as a fiberscope, that couples to visualization system 231. The image capture instrument may be single or multi-spectral, for example capturing image data in one or more of the visible, infrared, and/or ultraviolet spectrums. Alternatively, medical instrument 226 may itself be the image capture probe. Medical instrument 226 may be advanced from the opening of channel 221 to perform the procedure and then retracted back into the channel when the procedure is complete. Medical instrument 226 may be removed from proximal end 217 of flexible body 216 or from another optional instrument port (not shown) along flexible body 216.

Medical instrument 226 may additionally house cables, linkages, or other actuation controls (not shown) that extend between its proximal and distal ends to controllably the bend distal end of medical instrument 226. Steerable instruments are described in detail in U.S. Pat. No. 7,316,681 (filed on Oct. 4, 2005) (disclosing "Articulated Surgical Instrument for Performing Minimally Invasive Surgery with Enhanced Dexterity and Sensitivity") and U.S. patent application Ser. No. 12/286,644 (filed Sep. 30, 2008) (disclosing "Passive Preload and Capstan Drive for Surgical Instruments"), which are incorporated by reference herein in their entireties.

Flexible body 216 may also house cables, linkages, or other steering controls (not shown) that extend between drive unit 204 and distal end 218 to controllably bend distal end 218 as shown, for example, by broken dashed line depictions 219 of distal end 218. In some examples, at least four cables are used to provide independent "up-down" steering to control a pitch of distal end 218 and "left-right" steering to control a yaw of distal end 281. Steerable catheters are described in detail in U.S. patent application Ser. No. 13/274,208 (filed Oct. 14, 2011) (disclosing "Catheter with Removable Vision Probe"), which is incorporated by reference herein in its entirety. In embodiments in which medical instrument system 200 is actuated by a teleoperational assembly, drive unit 204 may include drive inputs that removably couple to and receive power from drive elements, such as actuators, of the teleoperational assembly. In some embodiments, medical instrument system 200 may include gripping features, manual actuators, or other components for manually controlling the motion of medical instrument system 200. Elongate device 202 may be steerable or, alternatively, the system may be non-steerable with no integrated mechanism for operator control of the bending of distal end 218. In some examples, one or more lumens, through which medical instruments can be deployed and used at a target surgical location, are defined in the walls of flexible body 216.

In some embodiments, medical instrument system 200 may include a flexible bronchial instrument, such as a bronchoscope or bronchial catheter, for use in examination, diagnosis, biopsy, or treatment of a lung. Medical instrument system 200 is also suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from tracking system 230 may be sent to a navigation system 232 where it is combined with information from visualization system 231 and/or the preoperatively obtained models to provide the physician, clinician, or surgeon or other operator with real-time position information. In some examples, the real-time position information may be displayed on display system 110 of FIG. 1 for use in the control of medical instrument system 200. In some examples, control system 116 of FIG. 1 may utilize the position information as feedback for positioning medical instrument system 200. Various systems for using fiber optic sensors to register and display a surgical instrument with surgical images are provided in U.S. patent application Ser. No. 13/107,562, filed May 13, 2011, disclosing, "Medical System Providing Dynamic Registration of a Model of an Anatomic Structure for Image-Guided Surgery," which is incorporated by reference herein in its entirety.

In some examples, medical instrument system 200 may be teleoperated within medical system 100 of FIG. 1. In some embodiments, teleoperational manipulator assembly 102 of FIG. 1 may be replaced by direct operator control. In some examples, the direct operator control may include various handles and operator interfaces for hand-held operation of the instrument.

Figure 3A:
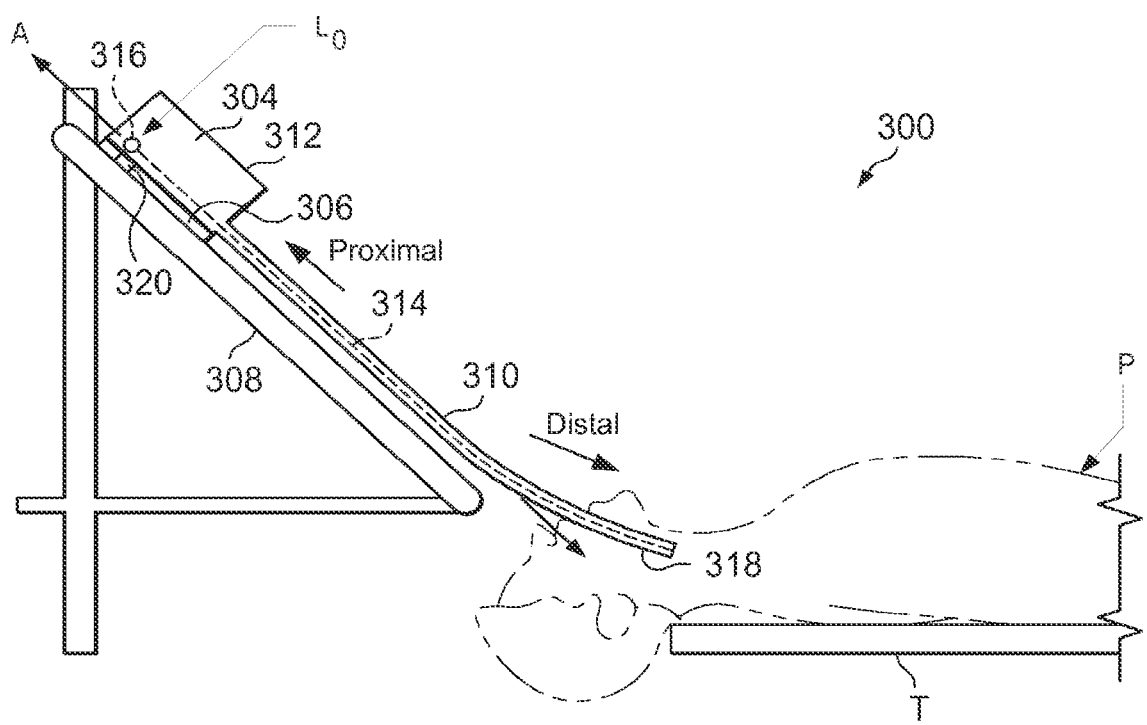
FIGS. 3A and 3B are simplified diagrams of side views of a patient coordinate space including a medical instrument mounted on an insertion assembly according to some embodiments.
Figure 3B:
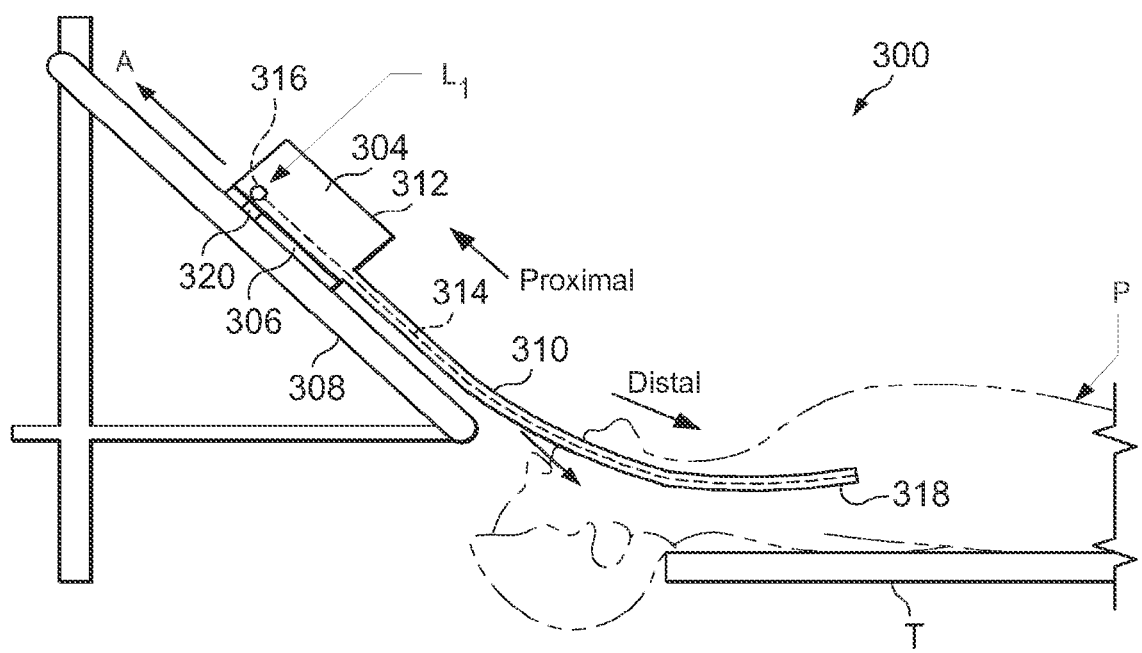

FIGS. 3A and 3B are simplified diagrams of side views of a patient coordinate space including a medical instrument mounted on an insertion assembly according to some embodiments. As shown in FIGS. 3A and 3B, a surgical environment 300 includes a patient P is positioned on platform 302. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within surgical environment 300, a point gathering instrument 304 is coupled to an instrument carriage 306. In some embodiments, point gathering instrument 304 may use EM sensors, shape-sensors, and/or other sensor modalities. Instrument carriage 306 is mounted to an insertion stage 308 fixed within surgical environment 300. Alternatively, insertion stage 308 may be movable but have a known location (e.g., via a tracking sensor or other tracking device) within surgical environment 300. Instrument carriage 306 may be a component of a teleoperational manipulator assembly (e.g., teleoperational manipulator assembly 102) that couples to point gathering instrument 304 to control insertion motion (i.e., motion along the A axis) and, optionally, motion of a distal end 318 of an elongate device 310 in multiple directions including yaw, pitch, and roll. Instrument carriage 306 or insertion stage 308 may include actuators, such as servomotors, (not shown) that control motion of instrument carriage 306 along insertion stage 308.

Elongate device 310 is coupled to an instrument body 312. Instrument body 312 is coupled and fixed relative to instrument carriage 306. In some embodiments, an optical fiber shape sensor 314 is fixed at a proximal point 316 on instrument body 312. In some embodiments, proximal point 316 of optical fiber shape sensor 314 may be movable along with instrument body 312 but the location of proximal point 316 may be known (e.g., via a tracking sensor or other tracking device). Shape sensor 314 measures a shape from proximal point 316 to another point such as distal end 318 of elongate device 310. Point gathering instrument 304 may be substantially similar to medical instrument system 200.

A position measuring device 320 provides information about the position of instrument body 312 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of instrument body 312. In some embodiments, insertion stage 308 is linear. In some embodiments, insertion stage 308 may be curved or have a combination of curved and linear sections.

FIG. 3A shows instrument body 312 and instrument carriage 306 in a retracted position along insertion stage 308. In this retracted position, proximal point 316 is at a position L0 on axis A. In this position along insertion stage 308 an A component of the location of proximal point 316 may be set to a zero and/or another reference value to provide a base reference to describe the position of instrument carriage 306, and thus proximal point 316, on insertion stage 308. With this retracted position of instrument body 312 and instrument carriage 306, distal end 318 of elongate device 310 may be positioned just inside an entry orifice of patient P. Also in this position, position measuring device 320 may be set to a zero and/or the another reference value (e.g., I=0). In FIG. 3B, instrument body 312 and instrument carriage 306 have advanced along the linear track of insertion stage 308 and distal end 318 of elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position LX may further be used as an indicator of the distance or insertion depth to which distal end 318 of elongate device 310 is inserted into the passageways of the anatomy of patient P.

Figure 4:
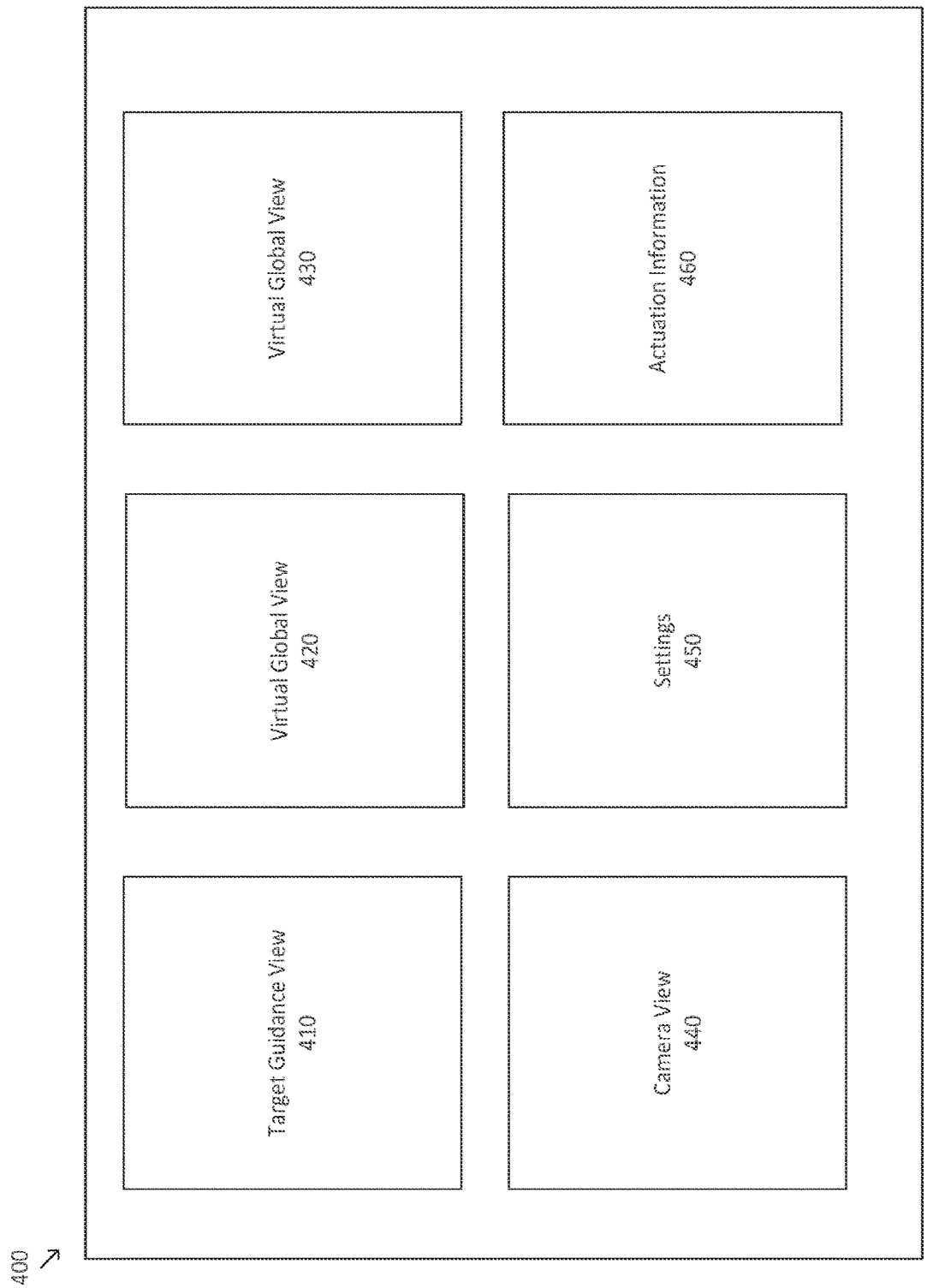
FIG. 4 is a simplified diagram of a graphical user interface for displaying supplemental guidance information for use in an image-guided surgical procedure according to some embodiments.

FIG. 4 is a simplified diagram of a graphical user interface 400 displayable on display system 110 according to some embodiments. In some embodiments consistent with FIGS. 1-3, graphical user interface 400 may be used to assist an operator, such as the physician, clinician, or surgeon O, during the operation and/or control of a medical instrument system, such as teleoperational manipulator assembly 100 and/or medical instrument system 200. Graphical user interface 400 displays information in one or more windows 410-460 that are viewable to the operator. Although six concurrently viewable windows on a single screen are depicted in FIG. 4, it is to be understood that graphical user interface 400 may display any suitable number of windows displayed on any suitable number of screens. In some examples, the number of concurrently viewable windows may be varied by opening and closing windows, minimizing and maximizing windows, moving windows between a foreground and background of graphical user interface 400, switching between screens, and/or otherwise fully or partially obscuring windows from view. Similarly, the arrangement of windows 410-460—including their size, shape, orientation, ordering (in case of overlapping windows), and/or the like—may vary and/or may be user-configurable.

According to some embodiments, windows 410-460 may display image data, sensor data, indicators, control modes, and/or any combination thereof. In some examples, image data may include pre-operative or intra-operative image data. Image data may be presented as two-dimensional, three-dimensional, or four-dimensional (including e.g., time based or velocity based information) live images and/or as images of calculated models created from pre-operative or intra-operative image data sets. In some examples, images of calculated models may be derived from sensor data, and may include models of instruments introduced into the anatomy. In some examples, the calculated models may be created from empirical data (in addition to or instead of image data) and/or may be based on a predetermined geometry of instruments and/or human anatomy. In some examples, indicators may include graphical and/or alphanumeric indicators. In some examples, controls may include buttons, text inputs, navigation panels, taskbars, icons, alerts, and/or the like. According to some embodiments, graphical user interface 400 may include a settings window 450 that displays available control modes, current control mode, and/or a list of settings associated with the medical instrument system.

As depicted in FIG. 4, one example of a graphical user interface 400 includes a target guidance window 410 and virtual global view windows 420 and 430 According to some embodiments, the data displayed in windows 410-430 may include virtual images generated by a virtual visualization system, such as virtual visualization system of control system 112.

Target guidance view window 410 displays a target location from a viewing angle corresponding to a distal end of the elongate device. According to some embodiments, target guidance view window 410 may display guidance information designed to assist the operator in steering the elongate device to the target location from close range.

Virtual global view windows 420 and 430 display virtual image data from viewing angles that provide a global view of patient P. In this manner, virtual global view window 430 simulates the field of view of an observer, such as surgeon O. In some examples, the virtual image data may display the real time position of the elongate device in the patient anatomy. In some examples, the respective viewing angles of virtual global view windows 470 and 480 may be selected manually and/or automatically. According to some embodiments, the respective viewing angles of virtual global view windows 470 and 480 may be rotated relative to each other. In some examples, the viewing angles have a fixed offset (e.g., a 90 degree offset to preserve orthogonality), such that rotating one of the perspectives causes the other to automatically rotate by a corresponding amount. In some examples, one or more of the viewing angles may be automatically selected to enhance the viewability of one or more bends in the elongate device. In some examples, one of the viewing angles may be automatically selected to match the view of a fluoroscopic imaging device used to observe the procedure. An embodiment of virtual global view windows 420 and 430 is discussed in greater detail below with reference to FIG. 5.

A camera view window 440 displays video image data captured by a visualization system, such as a visualization system of medical instrument 104. For example, the video image data may include video captured by an endoscope and/or a stereoscopic or monoscopic camera at or near a distal end of the medical instrument. One or more indicators and/or controls may be superimposed on and/or displayed alongside the image data to assist the operator in controlling the medical instrument.

When windows 410-440 are displayed concurrently, the images displayed in windows 410-440 advantageously allow the operator to concurrently monitor and/or visualize the vicinity of the distal end of the medical instrument (via target guidance window 410 and/or camera view window 440) as well as the three-dimensional pose of the medical instrument (via virtual global view windows 420 and 430) in relation to patient anatomy.

According to some embodiments, one or more of the images displayed in windows 410-440 may be augmented to display supplemental guidance information to the operator. Additionally, and/or alternately, graphical user interface 400 may display supplemental guidance information to the operator using an actuation information window 460. In some examples, the supplemental guidance information may be used to alert the operator to problems and/or potential problems that arise during the operation of the medical instrument. The supplemental guidance information may additionally provide assistance to the operator in correcting, avoiding, and/or alleviating a detected problem.

According to some embodiments, the supplemental guidance information may be associated with data from a tracking system, such as tracking system 230. The data from the tracking system may indicate a position, orientation, speed, velocity, pose, and/or shape of the elongate device and/or portions thereof. The data from the tracking system may further indicate chemical, biological, mechanical, and/or thermal conditions of the elongate device and/or portions thereof. For example, as discussed above with respect to FIG. 2A, the tracking system may include a shape sensor, such as shape sensor 222 and/or a fiber optic bend sensor, for determining the shape of an elongate device, such as elongate device 202. Data from the shape sensor may be used to further calculate specific conditions along the length of the elongate device (e.g. bend radius, buckling strain, activation force, temperature, and/or twist). Alternatively or additionally, the tracking system may include one or more application-specific sensors, such as temperature, force, strain gauge, electromagnetic, and/or pressure sensors, to measure conditions along the length of the elongate device. Such conditions could provide continuous supplemental guidance information or alerts to the operator when conditions reach a pre-determined threshold.

In one example, the supplemental guidance information may alert the operator to excessive bending of the elongate device detected by the tracking system. Whether an excessive bending condition exists may depend on the anatomy of the patient, such as patient P, the materials and/or design of the elongate device, the materials and/or design of a medical tool inserted into the elongate device, and/or the like. For example, excessive bending may be problematic because it prevents a medical tool inserted into the elongate device from reaching a distal end of the elongate device and/or may cause a kink to form in the elongate device. In some examples, a medical tool and/or a discrete portion of the medical tool inserted into the elongate device may be stiffer than the flexible body of the elongate device. Thus, when the elongate device is in a configuration where one or more portions of the elongate device are excessively bent, it may be difficult and/or impossible for the medical device to be delivered past the excessively bent portion(s). In furtherance of such examples, the supplemental guidance information may assist the operator in detecting and correcting the excessive bending condition prior to inserting the medical tool into the patient. This prevents the operator from repeatedly inserting and removing the medical tool from elongate device to manually discover by a "guess-and-check" method when one or more portions of the elongate device are excessively bent. According to some embodiments, the supplemental guidance information may alert the operator to a variety of other problems that arise during operation of the medical instrument system, such as buckling, excessive strain, excessive twist, excessive force, out of range temperature, blockages in an anatomical passageway, anomalies detected by the tracking system (e.g., anomalies in the chemical, biological, mechanical, and/or thermal environment of the elongate device), and/or the like.

Figure 5:
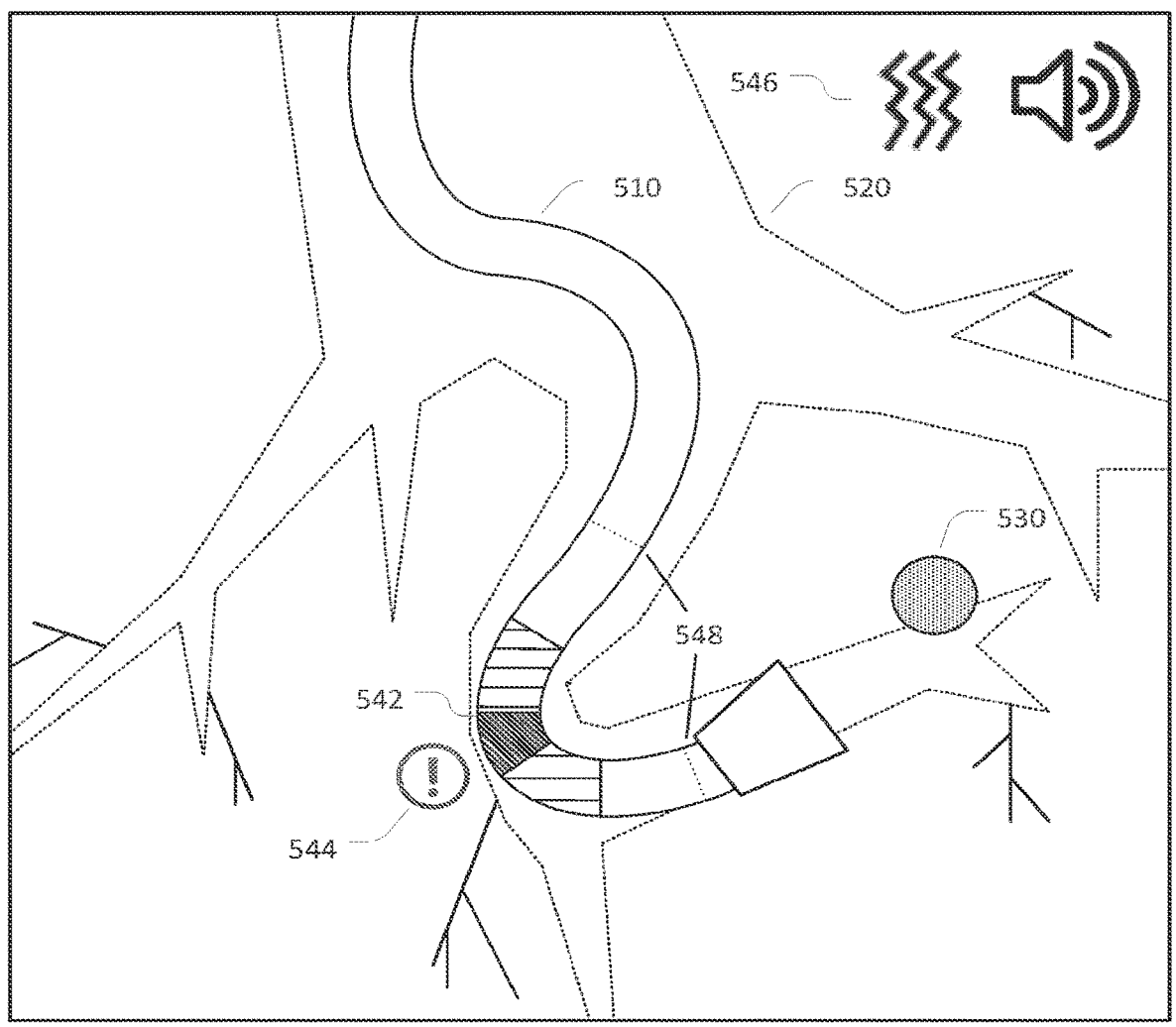
FIG. 5 is a simplified diagram of a window for displaying images augmented with supplemental guidance information according to some embodiments.

FIG. 5 is a simplified diagram of a window 500 for displaying virtual image data augmented with supplemental guidance information according to some embodiments. According to some embodiments consistent with FIGS. 1-4, window 500 may correspond to one or more of virtual global view windows 420 and 430. In this example, the image data in window 500 depicts an elongate device 510, anatomical features 520, and a target 530. According to some embodiments, anatomical features 520 may include anatomical features of interest, such as anatomical passageways, blood vessels, organs, and/or the like.

Target 530 identifies a point or region of the patient's anatomy where an operator intends to guide elongate device 510. As depicted in FIG. 5, target 530 is depicted as a sphere. According to some embodiments, target 530 may be omitted. For example, anatomical features 520 may provide sufficient guidance to the operator to steer elongate device 510 to a particular location even without target 530.

In some embodiments, image data that depicts elongate device 510, anatomical features 520, and target 530 may provide the operator with sufficient guidance information to steer elongate device 510 to a particular location within a patient, such as patient P. However, in many instances the operator may have difficulty detecting and correcting for problems encountered by elongate device 510 during insertion. For example, in some images, the operator may have difficulty determining the bend radius of elongate device 510 (and/or portions thereof) with precision. In some images, the operator may have difficulty distinguishing steerable portions of elongate device 510 from non-steerable portions. As a result, these images may be inadequate for controlling elongate device 510 in a manner that ensures that the bend radius of elongate device 510 does not exceed one or more predetermined threshold values. Similarly, even if the operator were to determine that elongate device 510 was excessively bent, conventional images may not provide sufficient guidance information for the operator to be able to correct the problem without resorting to inefficient methods such as "guess-and-check" to determine which direction to steer elongate device 510 to remedy the problem.

To address these deficiencies, the image data displayed in window 500 is augmented to display supplemental guidance information to the operator. Supplemental guidance information may be determined using a tracking system, such as a fiber optic bend sensor disposed along the length of elongate device 510 as previously described. In one embodiment, the supplemental guidance information is conveyed only when a pre-determined threshold is passed. In alternative embodiments, the supplemental guidance information may be conveyed to the operator continuously by way of a color scheme 542, an alert icon 544, haptic/audio alerts 546, structural indicators 548, numerical values and/or the like.

In one example, color scheme 542 indicates the bend radius of elongate device 510 at different positions along elongate device 510. Color scheme 542 can be used to display the measured bend radius by varying the color, texture, pattern, transparency, shade and/or another visual property of elongate device 510 as a function of position. Using color scheme 542, different colors and/or shades may be assigned to ranges of bend radius values (e.g., green may be assigned to a range that is considered straight and red may be assigned to a range that is considered bent, while yellow may be assigned to intermediate ranges). As depicted in FIG. 5, a color scheme is adopted in which darker portions of elongate device 510 correspond to a smaller bend radius. Such a color scheme may alert the operator to possible portions of elongate device 510 that are excessively bent. For example, a region of elongate device 510 may turn red when bent beyond a threshold value. According to some embodiments, the threshold value may correspond to a bend radius at which a medical tool, such as a needle, can no longer freely pass through elongate device 510. In some examples, the threshold value may correspond to a minimum bend radius of elongate device 510, such as a radius at which elongate device 510 becomes susceptible to forming kinks. In some embodiments, there may be multiple threshold values, with each threshold value triggering a different change in color scheme 542, such as a transition to a darker hue of red to indicate that a more extreme threshold has been exceeded. Although transitions between colors are depicted as being abrupt, it is to be understood that color scheme 542 may gradually transition between colors in some examples so that a property of color scheme 542, such as hue, brightness, and/or the like, is computed as a continuous function of the bend radius. In some examples, color scheme 542 may be applied along the entire length of elongate device 510. In some examples, color scheme 542 may be limited to a distal portion of elongate device 510, as a proximal portion of elongate device 510 may not be as susceptible as the distal portion to becoming excessively bent.

According to some embodiments, alert icon 544 may appear in window 500 when the bend radius exceeds one or more threshold values. As depicted in FIG. 5, alert icon 544 is positioned in the vicinity of the problem area to direct the attention of the operator to the region where excessive bending is identified. However, in some embodiments, alert icon 544 may appear at any position in window 500 such as adjacent the location along the length of elongate device 510 where the tight bend radius is measured. In some embodiments (not shown), alert icon 544 may display alphanumeric values that quantify the bend radius, and/or may visually represent the magnitude of the bend radius using a gauge, meter, and/or the like. In some embodiments, the size, color, and/or other attribute of alert icon 544 may be proportional to the magnitude of the bend radius. In some examples, alert icon 544 may include an arrow and/or other directional indicator to assist the operator in reducing the bend radius of elongate device 510.

According to some embodiments, haptic/audio alerts 546 and associated graphical icons may be used to alert the operator when the bend radius exceeds one or more threshold values. For example, a haptic alert may be transmitted by vibrating a control device used by the operator to control elongate device 510, such as a joystick, a trackball, and/or the like. An audio alert may include an alarm signal and/or a voiceover that states the type of problem encountered. Haptic/audio alerts 546 may help to draw the attention of the operator to window 500 when the bend radius exceeds one or more threshold values even if the operator is looking elsewhere.

According to some embodiments, the supplemental guidance information may include structural indicators 548. In general, structural indicators may indicate structural components of elongate device 510, such as a distal end of elongate device 510 and/or different segments of elongate device 510, as a visual aid to the operator. As depicted FIG. 5, structural indicators 548 include steerable range indicators that visually bookend a portion of elongate device 510, if any, that is steerable. In furtherance of such embodiments, structural indicators 548 may include lines and/or markers indicating positions along elongate device 510 at which a transition between steerable and non-steerable portions of elongate device 510 occurs. In some examples, structural indicators 548 may include arrows, crosshairs, and/or any other suitable indicator or set of indicators. In some embodiments, elongate device 510 may be depicted using color scheme 542 within the steerable range and using a normal color scheme (e.g. gray) outside of the steerable range. In some examples, a designated color may be used for structural indicators 548, such as blue.

According to some embodiments, various modifications may be made to window 500 to improve the clarity and/or prominence with which the supplemental guidance information is displayed. According to some embodiments, a viewing angle of window 500 may be selected to highlight the portion of elongate device 510 with the tightest bend radius. For example, the viewing angle may be dynamically selected to be orthogonal to the plane of the tightest bend radius. In some examples, anatomical features 520 and/or target 530 may not be displayed in window 500 so as not to draw attention from the supplemental guidance information included in window 500.

Figure 6:
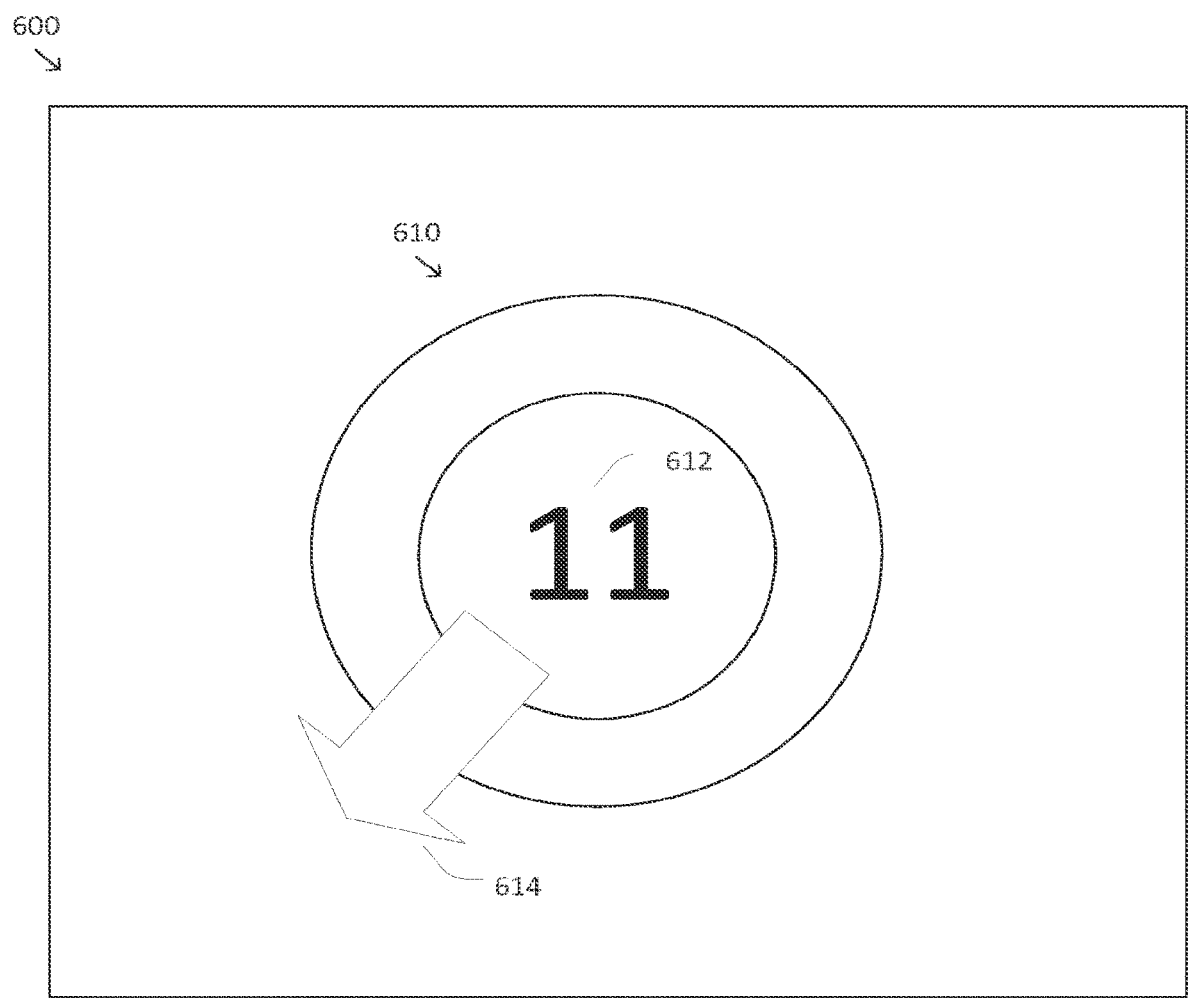
FIG. 6 is a simplified diagram of an actuation information window that displays actuation information including supplemental guidance information according to some embodiments.

FIG. 6 is a simplified diagram of a window 600 for displaying actuation information including supplemental guidance information according to some embodiments. According to some embodiments consistent with FIGS. 1-4, window 600 may correspond to actuation information window 460. Like the augmented images displayed in window 500, window 600 is used to display supplemental guidance information associated with a bend radius measured using a tracking system, such as a fiber optic bend sensor disposed along the length of an elongate device. According to some embodiments, window 600 may display one or more graphical indicators including an actuation information icon 610.

In general, actuation information icon 610 provides guidance information that assists an operator in correcting a problem encountered while controlling the elongate device, such as excessive bending of the elongate device. In some examples, actuation information icon 610 may include an alphanumeric indicator 612 that displays a minimum bend radius of the elongate device (i.e., the smallest bend radius along the length of the elongate device) to alert the operator to an excessive bending condition. In some examples, alphanumeric indicator 612 may display a numeric value which continually updates as the tightest bend radius changes but switches to an alpha value (e.g. YES or PASS) when the tightest bend radius equals a value that has been predetermined to safely allow the passage of a medical tool. In some examples, the value may be an alpha value that displays either a PASS or FAIL, YES or NO, and/or another binary indicator of a large enough bend radius down the length of the elongate device to allow for the passage of a medical tool.

In some examples, actuation information icon 610 may include a directional indicator 614, such as an arrow, that indicates which direction the operator should steer the elongate device to alleviate the excessive bending condition. In some examples, the color, size, texture, and/or other attributes of actuation information icon 610, alphanumeric indicator 612, and/or directional indicator 614 may be dynamic so as to convey supplemental guidance information to the operator. For example, different colors may correspond to different ranges of band radius (e.g., red corresponds to a bend radius of 1-10, green corresponds to a bend radius over 50, and yellow— and/or a gradually shifting shade of color from red to orange to yellow to green— corresponds to a bend radius of 11-49). In some examples, the color scheme used to determine the color of actuation information icon 610 may match color scheme 542 of window 500. The color scheme may be applied to action information icon 610 or portions of thereof such as directional indicator 614 and/or numerical indicator 612. In some examples, one or more of actuation information icon 610, alphanumeric indicator 612, and/or directional indicator 614 may disappear when excessive bending is not detected.

In the illustrative example depicted in FIG. 6, the minimum bend radius of the elongate device is 11 mm, as depicted by alphanumeric indicator 612. The smaller the number, the tighter the bend radius. In order to increase the minimum bend radius, the operator is instructed to navigate a control device, such as a joystick, a trackball, and/or the like, down and to the left, as depicted by the arrow of directional indicator 614. For example, in one or more embodiments, actuation information icon 610 may depict a top view of a trackball used by the operator to control the bend of a steerable portion of the elongate device. In furtherance of such embodiments, directional indicator 614 may indicate the direction the trackball should be rolled to straighten the steerable portion of the elongate device.

While the examples in FIGS. 4-6 have been largely described with respect to display of bend radius, it should be understood that the display in any of the previously described examples can similarly represent conditions such as but not limited to buckling strain, activation force, temperature, and/or twist. As with bend, buckling, strain, activation force, temperature, and/or twist may be displayed as varying colors, textures, patterns, transparencies, shades, alpha-numeric indicators, haptic/audible/visual alerts and/or visual properties along the length of the elongate device or at any location in any of the previously described display windows.

Figure 7:
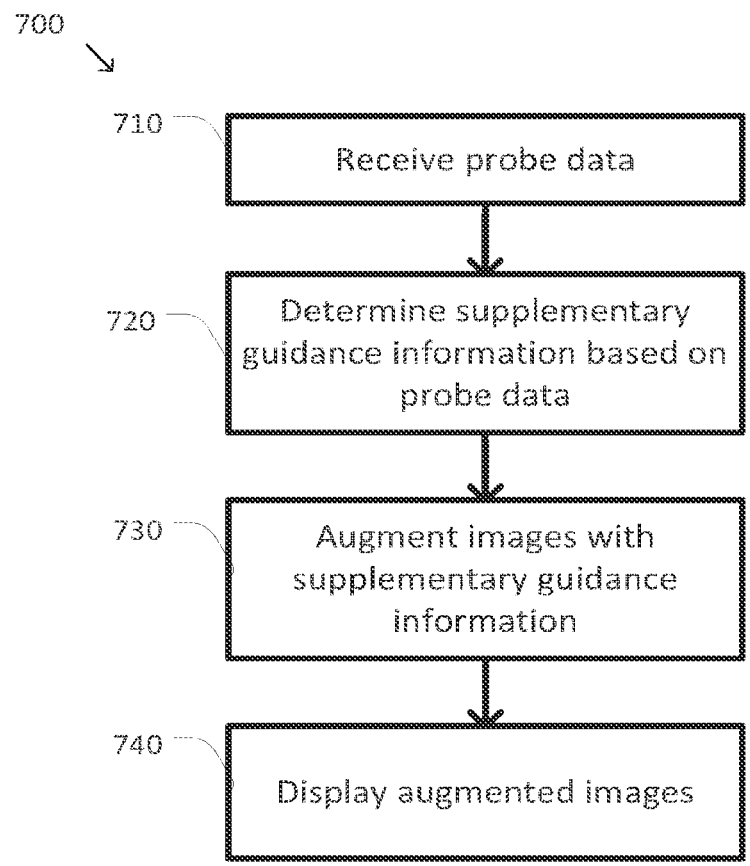
FIG. 7 is a simplified diagram of a method of displaying supplemental guidance information during an image-guided surgical procedure according to some embodiments.

FIG. 7 is a simplified diagram of a method 700 of displaying supplemental guidance information during an image-guided surgical procedure according to some embodiments. In some examples, method 700 may be used to display supplemental guidance information on a graphical user interface, such as graphical user interface 400, and/or in a window of a graphical user interface, such as windows 500 and/or 600. Method 700 is illustrated in FIG. 7 as a set of operations or processes 710-740. Not all of the illustrated processes 710-740 may be performed in all embodiments of method 700. Additionally, one or more processes that are not expressly illustrated in FIG. 7 may be included before, after, in between, or as part of the processes 710-740. In some embodiments, one or more of the processes 710-740 of method 700 may be implemented, at least in part, in the form of executable code stored on non-transitory, tangible, computer readable media that when run by one or more processors (e.g., the processors of control system 112) may cause the one or more processors to perform one or more of the processes 710-740.

At a process 710, tracking data is received from a tracking system associated with an elongate device, such as elongate device 202. According to some embodiments, the tracking data may include information associated with the position, orientation, speed, velocity, environment (e.g., chemical, thermal, and/or biological environment), temperature, force, pose, and/or shape of a flexible body of the elongate device. In some examples, the tracking data may include data collected from a plurality of points and/or segments along the length of the flexible body. In some examples, the tracking system may include a shape sensor, such as a fiber optic bend sensor disposed along the length of the flexible body. Consistent with such embodiments, the tracking data may include a bend radius of the flexible body at various positions along the flexible body and/or sufficient information from which to determine the bend radius. In additional embodiments, the tracking data may be used to calculate alternative conditions of the flexible body such as buckling, strain, activation force, temperature, or twist.

At a process 720, supplemental guidance information is determined based on the received tracking data. In some examples, the supplemental guidance information may be determined by comparing the probe data to one or more predetermined thresholds. For example, when the probe data includes a bend radius of the flexible body at various positions along the flexible body, the supplemental guidance may be determined by comparing the bend radius to a minimum allowable bend radius of the flexible body. In some examples, the minimum allowable bend radius may be selected to ensure the unimpeded passage of one or more medical devices through the flexible body. In some examples, the minimum allowable bend radius may be selected to prevent kinks or other damage to the flexible body.

In some examples, the minimum bend radius may be 10 mm or less. In some examples, one or more threshold values may be configurable (e.g., set by the operator) and/or may vary based on the type of surgical procedure, the model of the elongate device, the physical characteristics of the patient, the types of medical devices being inserted into the flexible body, and/or the like. According to some embodiments, the supplemental guidance information may additionally, and/or alternately, include corrective guidance information. For example, when the bend radius of the flexible body is smaller than a particular threshold, determining the corrective guidance information may include determining a direction in which to steer the flexible body in order to alleviate the excessive bending condition.

At a process 730, one or more images are augmented to include the supplemental guidance information. According to some embodiments, the one or more images may correspond to virtual global images generated by a virtual visualization system, such as virtual visualization system of control system 112. Consistent with such embodiments, supplemental guidance information may be input into the virtual visualization system to generate virtual images augmented using the supplemental guidance information. Alternately or additionally, virtual images may be received from the virtual visualization system, and the supplemental guidance information may be overlaid on the received virtual images. In some embodiments, the one or more images may correspond to video image data captured by a visualization system, such as a visualization system of medical instrument 104. Consistent with such embodiments, supplemental guidance information may be overlaid on the video image data. As discussed previously with respect to FIG. 5, the images may be augmented by including a color scheme, alert icon, haptic/audio indicator, structural indicators, and/or the like. In some examples, augmenting the one or more images may include applying a color scheme to the flexible body such that portions of the flexible body with a smaller bend radius are colored or shaded differently than portions of the flexible body with a larger bend radius. Similarly, augmenting the one or more images may include applying structural indicators to the flexible body to demarcate one or more portions of the flexible body that are steerable. In some examples, the supplemental guidance information may be displayed as actuation information, such as arrows indicating a direction in which to steer the flexible body of the elongate device in order to reduce the bend.

At a process 740, the one or more augmented images are displayed on the graphical user interface. In some examples, the one or more augmented images may be displayed in a window concurrently with a supplemental guidance window, such as supplemental guidance window 600. In some examples, the one or more augmented images may be displayed concurrently with an audio and/or haptic alert to indicate whether a threshold value is exceeded, such as when excessive bending of the flexible body is detected. In some examples, the one or more augmented images may be displayed concurrently with an actuation information icon. For example, the actuation information icon may include a directional indicator to display the direction to steer the flexible body to increase the bend radius.

Figure 8:
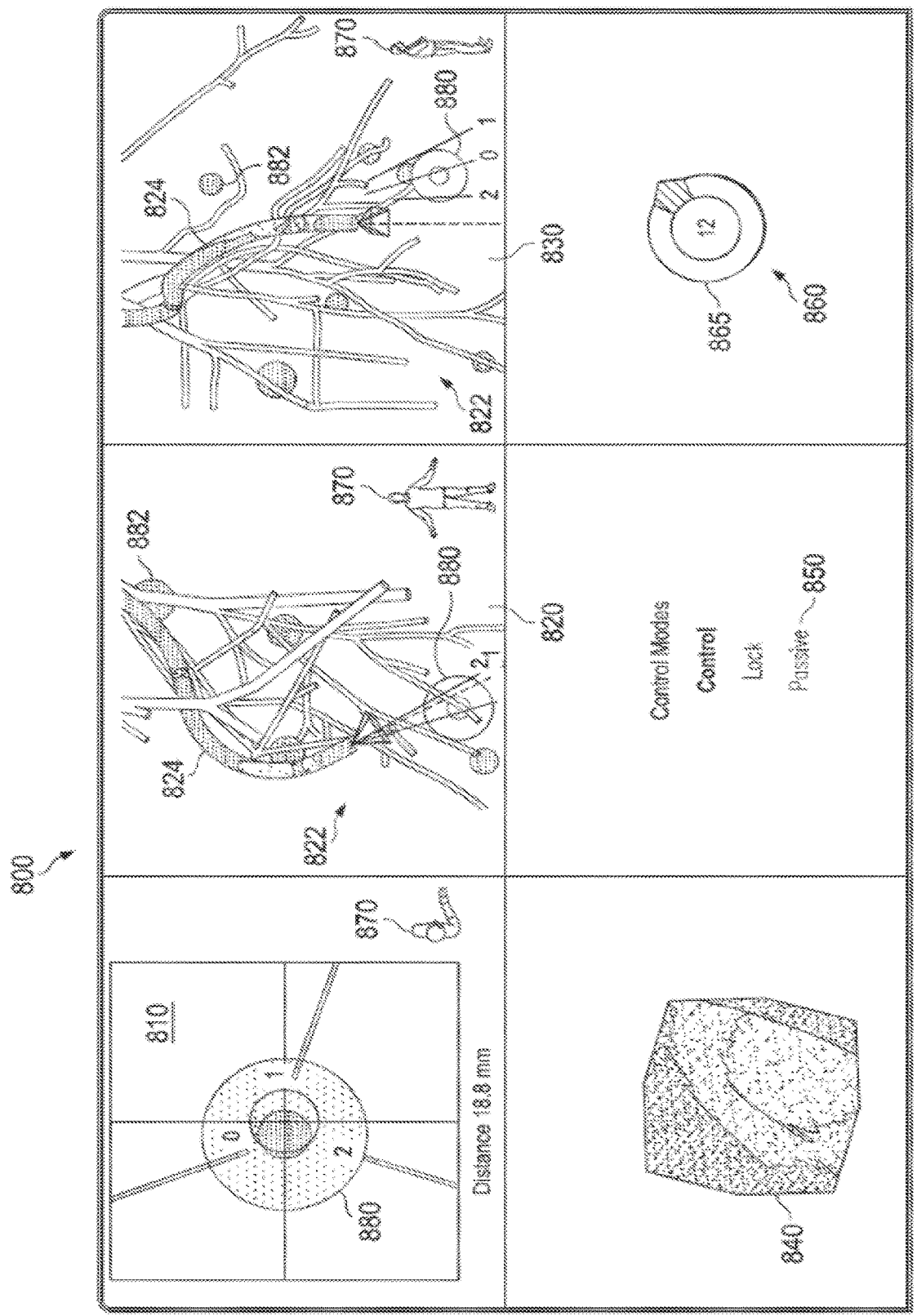
FIG. 8 is a screenshot of a graphical user interface displaying supplemental guidance information for use in an image-guided surgical procedure according to some embodiments.

FIG. 8 is a screenshot 800 of a graphical user interface displaying supplemental guidance information for use in an image-guided surgical procedure according to some embodiments. Like graphical user interface 400, screenshot 800 depicts six concurrently viewable frames or windows 810-860. The upper three frames 810-830 depict virtual images corresponding to a target guidance view and two virtual global views of an elongate device inserted into an anatomical passageway. Orientation indicators 870 are displayed in the lower right corner of each of the virtual images to indicate the viewing angle of each image relative to a patient. Virtual global views 820 and 830 illustrate a graphical representation of a 3D anatomical model 822 of a patient's lung and a model 824 of an elongate device as it moves through the branches of the lung. In some examples, 3D anatomical model 822 may be generated from preoperative CT scans and then registered to the patient's anatomy. Model 824 is also registered to the patient's anatomy, and the representation of the elongate device within model 824 is updated in real-time based on tracking data previously described. Additionally, a user pre-selected target 880 is displayed in frames 810-830.

Like the image displayed in window 500, the virtual global images 820 and 830 are augmented to display supplemental guidance information. More specifically, model 824 of the elongate device is colored according to a color scheme that indicates the bend radius of the elongate device at each point along its length. A red portion of model 824 indicates that the bend radius in that portion is within a critical range (e.g., below a predetermined threshold value) where there is a risk of blocking the passage of an instrument through the elongate device and/or straining the elongate, while green is assigned to portions of the elongate device that are deemed to be outside the critical range and not problematic in terms of passage of an instrument and/or strain on the elongate device. In this particular example, red corresponds to a bend radius of 1-10, green corresponds to a bend radius over 50, and a gradually shifting shade of color from red to orange to yellow to green corresponds to a bend radius of 11-49. In addition, the blue lines on model 824 demarcate a portion of the elongate device that is steerable. Portions of elongate device in between the blue line are steerable; other portions are not steerable.

The lower three frames or windows depicted in screenshot 800 include an endoscopic camera window 840, a control mode window 850, and an actuation information window 860. Like actuation information window 600, actuation information window 860 includes an actuation information icon 865 that depicts a top view of a trackball used by the operator. Actuation information icon 865 alphanumerically indicates the minimum bend radius of the elongate device and graphically indicates the direction in which to steer the elongate device (i.e., the direction the operator should roll the trackball) to increase the minimum bend radius and mitigate the excessive bending. The color of actuation information icon 865 is dynamic and matches the color scheme of model 824: red corresponds to a minimum bend radius of 1-10, green corresponds to a minimum bend radius over 50, and a gradually shifting shade of color from red to orange to yellow to green corresponds to a minimum bend radius of 11-49.

Based on the color scheme of model 824, the color scheme of actuation information icon 865, and/or the alphanumeric bend radius indicator of actuation information icon 865, the operator may observe an excessive bending condition of the elongate device. Moreover, the operator may observe an abrupt change in the bend of the elongate device at a position where the expected shape of the elongate device is straight, such as at a position within or near a straight branch of an anatomical passageway. Based on these observations, the operator may reposition the elongate device manually and/or robotically using a trackball, particularly when the operator believes the displayed information indicates a minor and/or fixable problem. Alternately or additionally, the operator may withdraw the elongate device partially and attempt a different approach to the target, and/or entirely withdraw the elongate device from the patient, particularly when the operator believes the displayed information indicates a severe and/or dangerous failure. In some examples, this process may allow the operator to remove the elongate device from the patient before inserting a medical tool into the elongate device, thereby preventing the failure from being exacerbated by inserting the medical tool into a region where an undetected failure exists. In one or more embodiments, one or more threshold values for bend radius may be used to assist the operator in determining the severity of the excessive bending condition and the appropriate mitigating actions to take.

Figure 9:
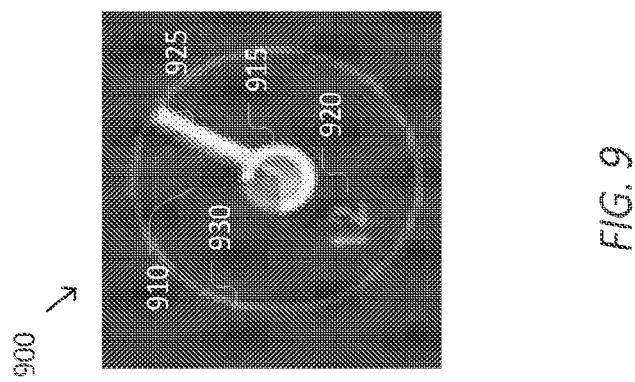
FIG. 9 is a simplified diagram of a bend indicator according to some embodiments.

FIG. 9 is a simplified diagram of a bend indicator 900 according to some embodiments. According to some embodiments consistent with FIGS. 1-8, bend indicator 900 may be displayed in actuation information window 460. In some examples, bend indicator 900 may be displayed alongside an actuation information icon, such as actuation information icon 610, and/or as an alternative to the actuation information icon. However, it is to be understood that bend indicator 900 may be displayed in contexts other than graphical user interface 400, including as a standalone view and/or in conjunction with views other than those depicted in graphical user interface 400. In some examples, bend indicator 900 may appear when a tight bend radius is detected in the catheter (e.g., when the bend radius is below a predetermined threshold) and may be hidden otherwise. Alternatively, selected portions of bend indicator 900 may be hidden when no tight bend is present, e.g. numerical bend radius 910.

Bend indicator 900 provides a schematic bend representation 910 of the catheter. When the distal tip of the catheter is bent, a bend line 925 appears which indicates the direction the catheter distal end is bending. For example, as depicted in FIG. 9, the bend line 925 appears on the upper right of a ring 915, indicating that the catheter is bent to the right. Thus to straighten the catheter, the catheter may be steered to the lower left to reduce the bend. In some examples, when the catheter distal end is straight, bend line 925 may be hidden.

In some examples, schematic bend representation 910 may include a rendering of a distal end of the catheter from the perspective of looking backwards up the catheter tube through a distal tip of the catheter (towards a proximal portion of the catheter from the distal tip). Consistent with such examples, ring 915 may be interpreted as corresponding to the distal tip of the catheter. When the catheter is bent, portions of the catheter become visible behind the distal tip (i.e., ring 915). Consequently, bend line 925 may correspond to the portions of the distal end of the catheter that are visible behind the distal tip (i.e., ring 915) due to the bending of the catheter.

In alternative examples, schematic bend representation 910 may include a rendering of the distal end of the catheter from the perspective of looking forward down the catheter tube towards the distal tip from a proximal position along the catheter. Consistent with such examples, ring 915 may be interpreted as corresponding to a cross-sectional cut of the catheter at the proximal position. When the catheter is bent, portions of the distal end become visible behind the cross-sectional cut (i.e., ring 915). Consequently, bend line 925 may correspond to the portions of the catheter that are visible behind the cross-sectional cut (i.e., ring 915) due to the bending of the catheter.

In some examples, bend indicator 900 may display a visual and/or alphanumeric representation of the minimum bend radius or the smallest bend radius detected along the catheter. When the minimum bend radius drops below a threshold value, bend indicator 900 may alert the clinician that the predetermined threshold has been breached by displaying an alphanumeric value and/or may otherwise changing in appearance. In some embodiments, the threshold value may be determined based on whether a tool can be passed through the catheter. In some embodiments, the threshold value may be determined based on the radius at which buckling and/or damage to the catheter may occur. The threshold value may be manually selected, automatically determined, determined based on the type of catheter and/or tool, and/or set using a general rule of thumb. As depicted in FIG. 9, when the minimum detected bend radius is below the threshold value, bend indicator 900 includes a number 920 indicating the real-time value of the minimum bend radius, and portions of bend indicator 900 turn a different color, such as red as shown in FIG. 9.

In some embodiments, the location of the red colored portions may reflect the magnitude of the force applied by one of the motor to a catheter pull wire in that section of the catheter. For example, in FIG. 9 the pull wire on the top left is being pulled harder, as indicated by the red colored wedge appearing in schematic bend representation 910. In some examples, bend indicator 900 may include an outer ring 930 that dynamically changes color based whether the minimum bend radius is approaching or exceeds the threshold value. In some examples, dynamic changes could be represented by changes in appearance of portions of the bend indicator 900 in transparency, texture, line width, and/or color etc.

Some examples of control units, such as control unit 130 may include non-transient, tangible, machine readable media that include executable code that when run by one or more processors (e.g., processor 140) may cause the one or more processors to provide the graphical user interface 400 or perform the processes of method 700. Some common forms of machine readable media that may provide the graphical user interface 400 or include the processes of method 700 are, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

ADDITIONAL EXAMPLES

A. A non-transitory machine-readable medium comprising a plurality of machine-readable instructions which when executed by one or more processors associated with a medical device are adapted to cause the one or more processors to perform a method comprising:

receiving tracking data associated with an elongate device;

calculating at least one condition along a length of the elongate device based on the tracking data;

determining supplemental guidance information based on the at least one condition;

augmenting one or more images including a graphical representation of the elongate device with the supplemental guidance information to produce one or more augmented images; and displaying the one or more augmented images on a display device at a surgeon console.

B. The non-transitory machine-readable medium of example A, wherein the tracking data is received from a tracking system includes a shape sensor.

C. The non-transitory machine-readable medium of example B, wherein the shape sensor includes a fiber optic bend sensor.

D. The non-transitory machine-readable medium of any one of examples A-C, wherein the at least one condition further comprises at least one of a bend radius, buckling condition, strain, activation force, temperature, and twist of a flexible body of the elongate device.

E. The non-transitory machine-readable medium of example D, wherein determining the supplemental guidance information includes determining whether the bend radius is less than a minimum allowable bend radius.

F. The non-transitory machine-readable medium of example E, wherein the minimum allowable bend radius is selected to allow passage of a medical device through the elongate device.

G. The non-transitory machine-readable medium of example E, wherein the minimum allowable bend radius is selected to prevent a kink or damage to the elongate device.

H. The non-transitory machine-readable medium of example D, wherein augmenting the one or more images includes applying a color scheme to the graphical representation of the elongate device, wherein portions of the graphical representation of the elongate device corresponding to a smaller bend radius are shaded differently than portions of the graphical representation of the elongate device corresponding to a larger bend radius.

I. The non-transitory machine-readable medium of any one of examples A-H, wherein the one or more images include structural indicators, the structural indicators demarcating one or more portions of the elongate device that are steerable.

J. The non-transitory machine-readable medium of any one of examples D-I, wherein the supplemental guidance information includes corrective guidance information.

K. The non-transitory machine-readable medium of example J, wherein the corrective guidance information includes a direction to steer the elongate device to increase the bend radius.

L. The non-transitory machine-readable medium of example K, wherein the method further comprises displaying actuation information on the display device, the actuation information including a directional indicator to display the direction to steer the flexible body to increase the bend radius.

M. The non-transitory machine-readable medium of any one of examples A-L, wherein the one or more images include one or more virtual images.

N. The non-transitory machine-readable medium of any one of examples A-L, wherein the one or more images include one or more video images.

O. The non-transitory machine-readable medium of example A, wherein the method performed by the one or more processors further comprises identifying at least one of a position, an orientation, a speed, a velocity, an chemical environment, a thermal environment, a biological environment, a pose, and a shape of the elongate device from the tracking data.

P. The non-transitory machine-readable medium of claim O, wherein the at least one of the position, the orientation, the speed, the velocity, the chemical environment, the thermal environment, the biological environment, the pose, and the shape is measured at a plurality of positions along the length of the elongate device.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method for displaying guidance information, the method comprising:

receiving, by one or more hardware processors, data from a tracking system associated with an elongate device comprising a flexible body;

determining, by the one or more hardware processors and based on the received data, a buckling condition along a length of the flexible body;

determining, by the one or more hardware processors and based on the buckling condition, supplemental guidance information;

augmenting, by the one or more hardware processors, one or more images with the supplemental guidance information to produce one or more augmented images;

displaying the one or more augmented images on a display device at a surgeon console;

determining a direction to steer the flexible body to alleviate the buckling condition; and displaying a directional indicator informing a user of the determined direction.

2. The method of claim 1, wherein determining the buckling condition comprises comparing a bend radius along the length of the flexible body to a predetermined threshold value associated with buckling.

3. The method of claim 1, wherein the tracking system includes a shape sensor.

4. The method of claim 3, wherein the shape sensor includes a fiber optic bend sensor.

5. The method of claim 1, wherein the one or more images include structural indicators, the structural indicators demarcating one or more portions of the flexible body that are steerable.

6. The method of claim 1, wherein the supplemental guidance information includes corrective guidance information.

7. The method of claim 1, wherein the one or more images include virtual images.

8. The method of claim 1, wherein data from the tracking system is further associated with at least one of a position, an orientation, a speed, a velocity, a chemical environment, a thermal environment, a biological environment, a pose, or a shape of the elongate device.

9. A medical system comprising:
an elongate device including a flexible body;
a tracking system disposed along at least a portion of the flexible body;
a display device; and
one or more processors coupled to the tracking system;
wherein the one or more processors are configured to:
receive data from the tracking system;
based on the received data, determine a buckling condition along a length of the flexible body;
based on the buckling condition, determine supplemental guidance information including a direction to steer the flexible body to alleviate the buckling condition;
using the supplemental guidance information, augment one or more images to produce one or more augmented images; and
display the one or more augmented images on the display device.

10. The medical system of claim 9, wherein the tracking system includes a shape sensor.

11. The medical system of claim 10, wherein the shape sensor includes a fiber optic bend sensor.

12. The medical system of claim 9, wherein the one or more images include structural indicators, the structural indicators demarcating one or more portions of the flexible body that are steerable.

13. The medical system of claim 9, wherein the one or more images include one or more virtual images.

14. The medical system of claim 9, wherein the one or more images include one or more video images.

15. The medical system of claim 9, wherein the one or more processors are further configured to identify at least one of a position, an orientation, a speed, a velocity, a chemical environment, a thermal environment, a biological environment, a pose, or a shape of the elongate device from the data received from the tracking system.

* * * * *